(12) United States Patent
Hayenga et al.

(10) Patent No.: US 6,431,212 B1
(45) Date of Patent: Aug. 13, 2002

(54) VALVE FOR USE IN MICROFLUIDIC STRUCTURES

(76) Inventors: Jon W. Hayenga, 5310 240th Ave. NE., Redmond, WA (US) 98052; Clinton L. Williams, 2422 E. McGraw, Seattle, WA (US) 98112

( * ) Notice: Subject to any disclaimer, the term of this patent is extended or adjusted under 35 U.S.C. 154(b) by 0 days.

(21) Appl. No.: 09/677,250

(22) Filed: Oct. 2, 2000

Related U.S. Application Data

(60) Provisional application No. 60/206,878, filed on May 24, 2000.

(51) Int. Cl.[7] ............................ F16K 15/16; F16K 31/02
(52) U.S. Cl. ................. 137/855; 251/129.06; 251/61.1; 417/566; 417/413.2; 417/322
(58) Field of Search .................... 137/855, 856; 417/560, 413.1, 566, 322, 413.2; 251/129.06, 61.1

(56) References Cited

U.S. PATENT DOCUMENTS

| | | | |
|---|---|---|---|
| 2,856,955 A | * 10/1958 | Winkelman | 137/855 X |
| 3,807,444 A | * 4/1974 | Fortune | 137/855 X |
| 4,895,500 A | 1/1990 | Hok et al. | |
| 4,951,617 A | * 8/1990 | Linamen et al. | 137/855 X |
| 5,443,890 A | 8/1995 | Ohman | |
| 5,542,821 A | * 8/1996 | Dugan | 417/322 X |
| 5,564,911 A | * 10/1996 | Santa | 417/566 X |
| 5,593,130 A | 1/1997 | Hansson et al. | |
| 5,839,472 A | * 11/1998 | Shintoku et al. | 137/855 X |
| 5,899,218 A | * 5/1999 | Dugan | 137/855 X |
| 5,932,799 A | 8/1999 | Moles | |
| 5,962,081 A | 10/1999 | Ohman et al. | |
| 5,971,355 A | 10/1999 | Biegelsen et al. | |
| 6,033,191 A | 3/2000 | Kamper | |
| 6,068,751 A | 5/2000 | Neukermans | |

FOREIGN PATENT DOCUMENTS

| | | |
|---|---|---|
| DE | 195334378 C1 | 1/1997 |
| EP | 0518524 A2 | 12/1992 |

OTHER PUBLICATIONS

Gravesen et al., Microfluidics –A Review, Micromech, Microeng.3 (1993) 168–182.
Olsson, "Valveless Diffusion Micropumps", Ph.D. Thesis, KTH, Dep of Signals, Sensors, And Systems, TRITA–ILA–9803 ISSN: 0281–2878.

* cited by examiner

Primary Examiner—Kevin Lee
(74) Attorney, Agent, or Firm—Jerrold J. Litzinger

(57) ABSTRACT

A valve for use in laminated plastic microfluidic structures. The valve comprises first, second, and third layers of flexible material separated by first and second spacing layers to form microfluidic channels, and having an actuator section to selectively isolate the microfluidic channels from each other. The structure can also be used as a recirculating pump.

21 Claims, 4 Drawing Sheets

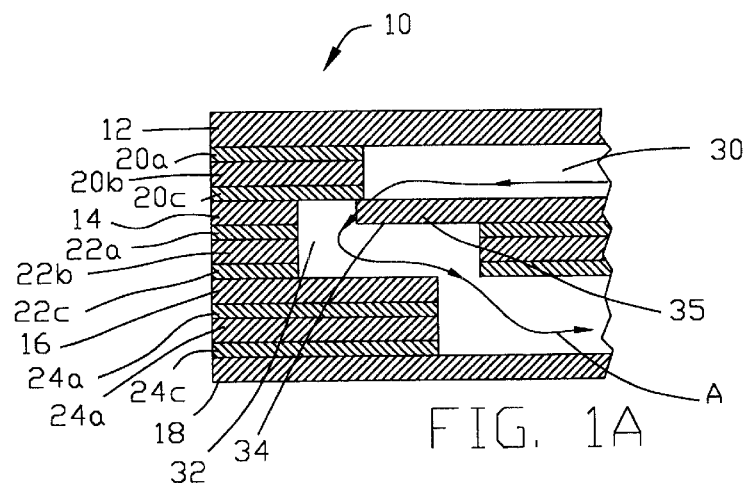
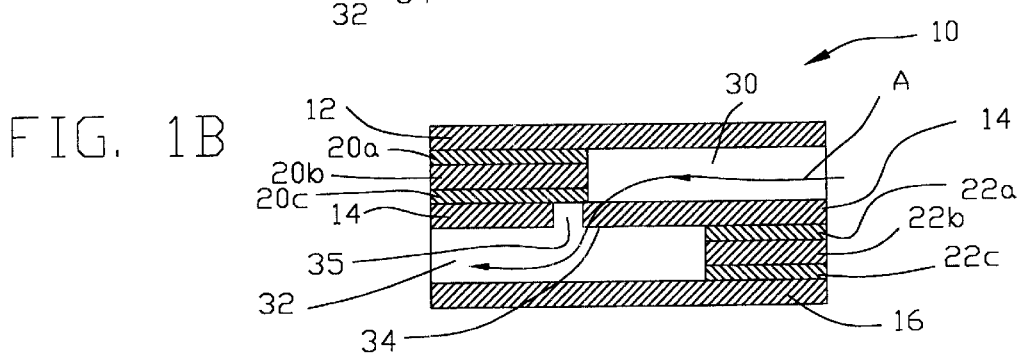
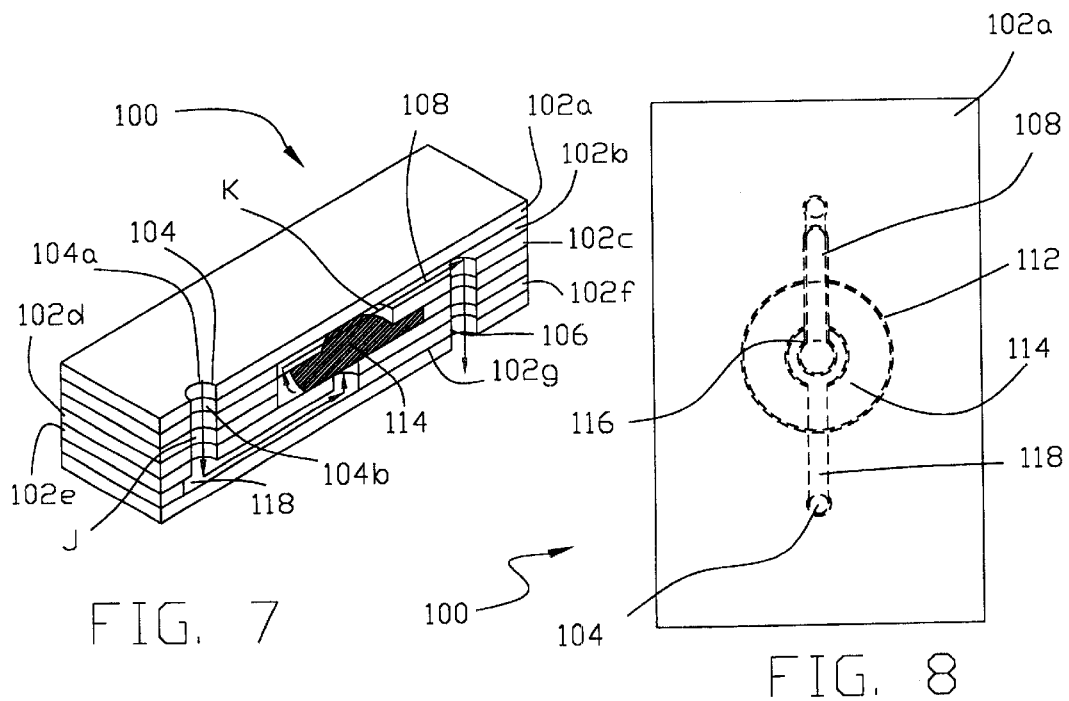

VALVE FOR USE IN MICROFLUIDIC STRUCTURES

CROSS-REFERENCE TO RELATED APPLICATIONS

This patent application is a continuation-in-part application of provisional U.S. Patent Application Serial No. 60/206,878, filed May 24, 2000, which application is incorporated herein by reference.

BACKGROUND OF THE INVENTION

1. Field of the Invention

This invention relates generally to microscale devices for performing analytical testing and, in particular, to a one-way valve for use in laminated plastic microfluidic structures.

2. Description of the Prior Art

Microfluidic devices have recently become popular for performing analytical testing. Using tools developed by the semiconductor industry to miniaturize electronics, it has become possible to fabricate intricate fluid systems which can be inexpensively mass produced. Systems have been developed to perform a variety of analytical techniques for the acquisition of information for the medical field.

Microfluidic devices may be constructed in a multi-layer laminated structure where each layer has channels and structures fabricated from a laminate material to form microscale voids or channels where fluids flow. A microscale channel is generally defined as a fluid passage which has at least one internal cross-sectional dimension that is less than 500 μm and typically between about 0.1 μm and about 500 μm. The control and pumping of fluids through these channels is affected by either external pressurized fluid forced into the laminate, or by structures located within the laminate.

Many different types of valves for use in controlling fluids in microscale devices have been developed. U.S. Pat. No. 4,895,500, which issued on Jan. 23, 1990, describes a silicon micromechanical non-reverse valve which consists of a cantilever beam extending over a cavity and integrally formed with the silicon wafer such that the beam can be shifted to control flow within channels of the microfluidic structure.

U.S. Pat. No. 5,443,890, which issued Aug. 22, 1995 to Pharmacia Biosensor AB, describes a sealing device in a microfluidic channel assembly having first and second flat surface members which when pressed against each other define at least part of a microfluidic channel system between them.

U.S. Pat. No. 5,593,130, which issued on Jan. 14, 1997 to Pharmacia Biosensor AB, describes a valve for use in microfluidic structures in which the material fatigue of the flexible valve membrane and the valve seat is minimized by a two-step seat construction and the fact that both the membrane and the seat are constructed from elastic material.

U.S. Pat. No. 5,932,799, which issued Aug. 3, 1999 to YSI Incorporated, teaches a microfluidic analyzer module having a plurality of channel forming laminate layers which are directly bonded together without adhesives, with a valve containing layer directly adhesivelessly bonded over the channel containing layers and a flexible valve member integral with the valve layer to open and close communication between feed and sensor channels of the network.

U.S. Pat. No. 5,962,081, which issued Oct. 5, 1999 to Pharmacia Biotech AB, describes a method for the manufacturer of polymer membrane-containing microstructures such as valves by combining polymer spin deposition methods with semiconductor manufacturing techniques.

U.S. Pat. No. 5,971,355, which issued on Oct. 26, 1999 to Xerox Corporation, describes a valve array system for microdevices based on microelectro-mechanical systems (MEMS) technology consisting of a dielectric material forming a laminate which is embedded within multiple laminate layers.

U.S. Pat. No. 6,068,751, which issued on May 30, 2000, describes a microfluidic delivery system using elongated capillaries that are enclosed along one surface by a layer of malleable material which is shifted by a valve having a electrically-powered actuator.

One-way valves, often called check valves, are commonly used in conventional fluid systems for controlling flow. These valves are capable of switching the resistance to fluid flow based upon the pressure developed in the fluid line. Forward pressure opens the valve and reverse pressure closes and seals the valve.

Several types of check valves are commonly used for fluid management in flow systems. Flap valves, ball-in-socket valves, and tapered wedge valves are a few of the valve types existing in the macroscale domain of fluid control. However, in the microscale field, where flow channels are often the size of a human hair (approximately 100 microns in diameter), there are special needs and uses for check valves which are unique to microscale systems, especially microfluidic devices incorporating fluids with various concentrations of particulate in suspension. Special challenges involve mixing, dilution, fluidic circuit isolation, and anti-sediment techniques when employing microscale channels within a device. The incorporation of a simple compact microfluidic flap valve within microscale devices addresses these potential problems while maintaining high density of fluidic structure within the device, and eliminating the need for active valve actuation in many cases.

SUMMARY OF THE INVENTION

It is therefore an object of the present invention to provide an efficient check valve suitable for use in a microfluidic system.

It is a further object of the present invention is to provide a microfluidic check valve which can be integrated into a cartridge constructed of multi-layer laminates.

It is a further object of the present invention is to provide an array of microfluidic check valves which can be integrated into a cartridge constructed of multi-layer laminates.

These and other objects of the present invention will be more readily apparent in the description and drawings which follow.

BRIEF DESCRIPTION OF THE DRAWINGS

FIG. 1A is a fragmentary cross-sectional view of a microfluidic device containing a basic check valve according to the present invention;

FIG. 1B is a fragmentary cross-sectional view of another microfluidic device containing a basic check valve;

FIG. 7 is a perspective view of another embodiment of an elastomeric check valve according to the present invention;

FIG. 8 is a top view, partly in phantom, of the valve shown in FIG. 7;

DETAILED DESCRIPTION OF THE PREFERRED EMBODIMENTS

Figure 2:
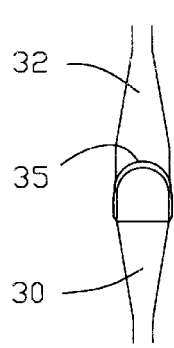
FIG. 2 is a top view of the valve of FIG. 1B partly in phantom.
Figure 3:
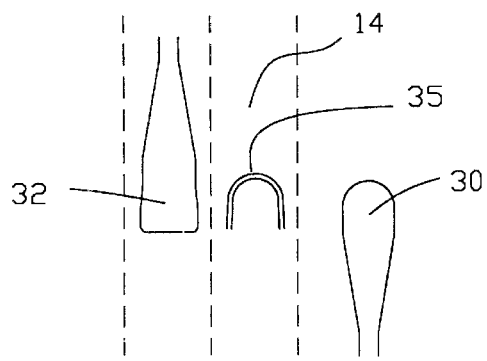
FIG. 3 is a view of the individual layers of the check valve shown in FIG. 1B.

Referring more particularly to FIGS. 1A and 1B of the drawings, there is shown a microfluidic assembly, generally indicated at 10, which contains a check valve which embodies the principles of the present invention. FIG. 1A illustrates assembly 10 having a top layer 12, a second layer 14, a third layer 16, and bottom layer 18. These layers are preferably formed from a thin flexible material such as MYLAR in the present embodiment, but could also be constructed from a more flexible material such as latex. Layers 12 and 14 are separated by a series of adhesive spacing sheets 20a–c. Layers 14 and 16 are separated by a series of adhesive spacing sheets 22a–c, while layers 16 and 18 are separated by a series of adhesive spacing sheets 24a–c. Assembly 10 shown in FIG. 1B only contains layers 12, 14, 16, separated by spacing sheets 20a–c and 22a–c respectively. Spacing sheets 20a–c, 22a–c, 24a–c are preferably constructed from a high performance adhesive such as ACA (Adhesive Carrier Adhesive) or PSA (Pressure Sensitive Adhesive) manufactured by 3M Company. In FIG. 1A, a first microfluidic chamber 30 is formed by sheets 20a–c separating layers 12 and 14. In FIG. 1A, a second microfluidics chamber 32 is formed within assembly 10 between layer 14 and layer 18, while chamber 32 is formed between layers 14 and 16 in FIG. 1B. Chambers 30 and 32 are separated by a flexible valve flap 34 which is formed within layer 14 by an opening 35, and which contacts the underside of sheet 20c. Flap 34 forms a one-way valve within assembly 10 as flap 34 can be flexed away from sheet 20c to create a passageway between chambers 30 and 32, but flap 34 cannot move in the opposite direction, therefore, forward pressure in channel 30 opens flap 34, while higher pressure in channel 32 seals flap 34 against sheet 20c. The direction of the flow pattern is shown by arrow A.

Devices such as assembly 10 can allow the introduction of two fluids together while preventing reverse flow of either fluid into the supply channel of the other fluid. This is important for maintaining correct fluid ratios within mixing systems, and also prevents contamination of reagents with sample, and vice-versa.

Another primary application for check valves in microfluidic systems is in recirculating pumps. The utilization of the compliance of the thin film layer within a multilayer laminate microfluidic device to pressurize a volume encapsulated within a pump chamber controls flow within the pump structure.

Figure 4:
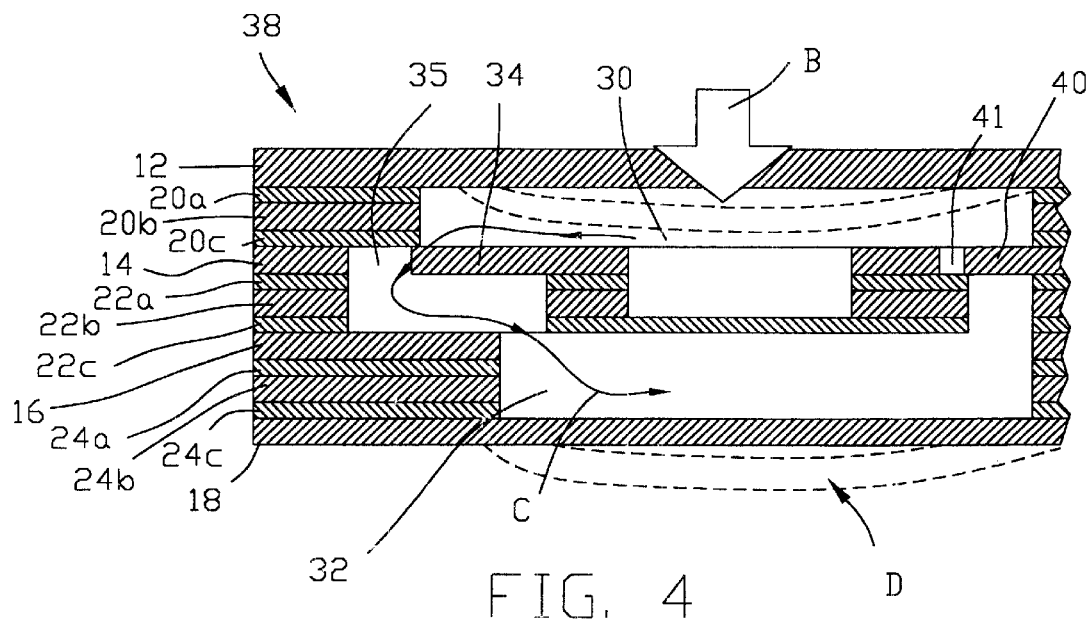
FIG. 4 is a fragmentary cross-sectional view of a microfluidic device containing a recirculating pump using a check valve according to the present invention showing its activated state.
Figure 5:
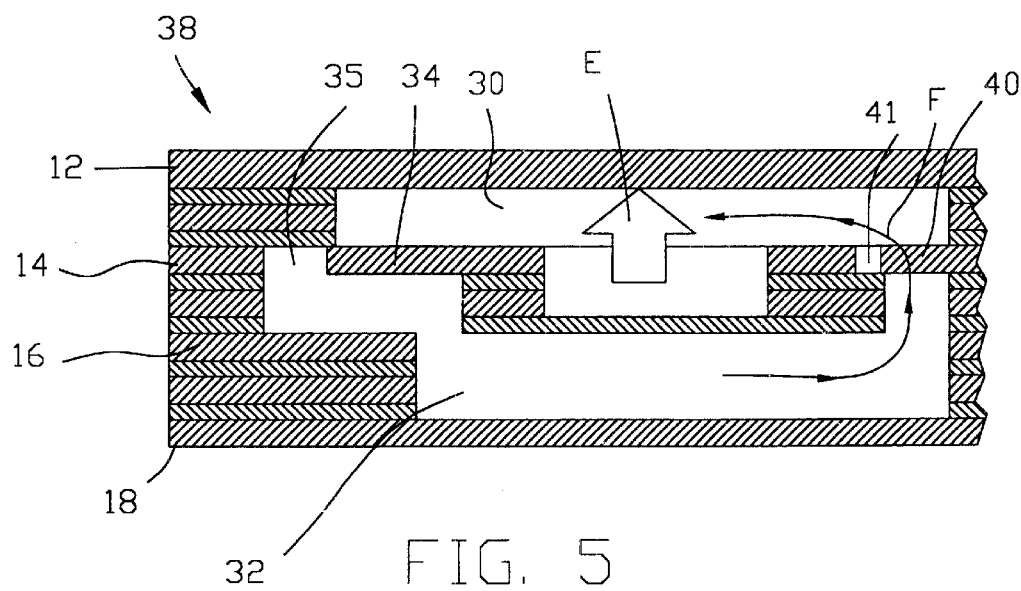
FIG. 5 is a view of FIG. 4 with the pump bellows in its relaxed position.
Figure 12:
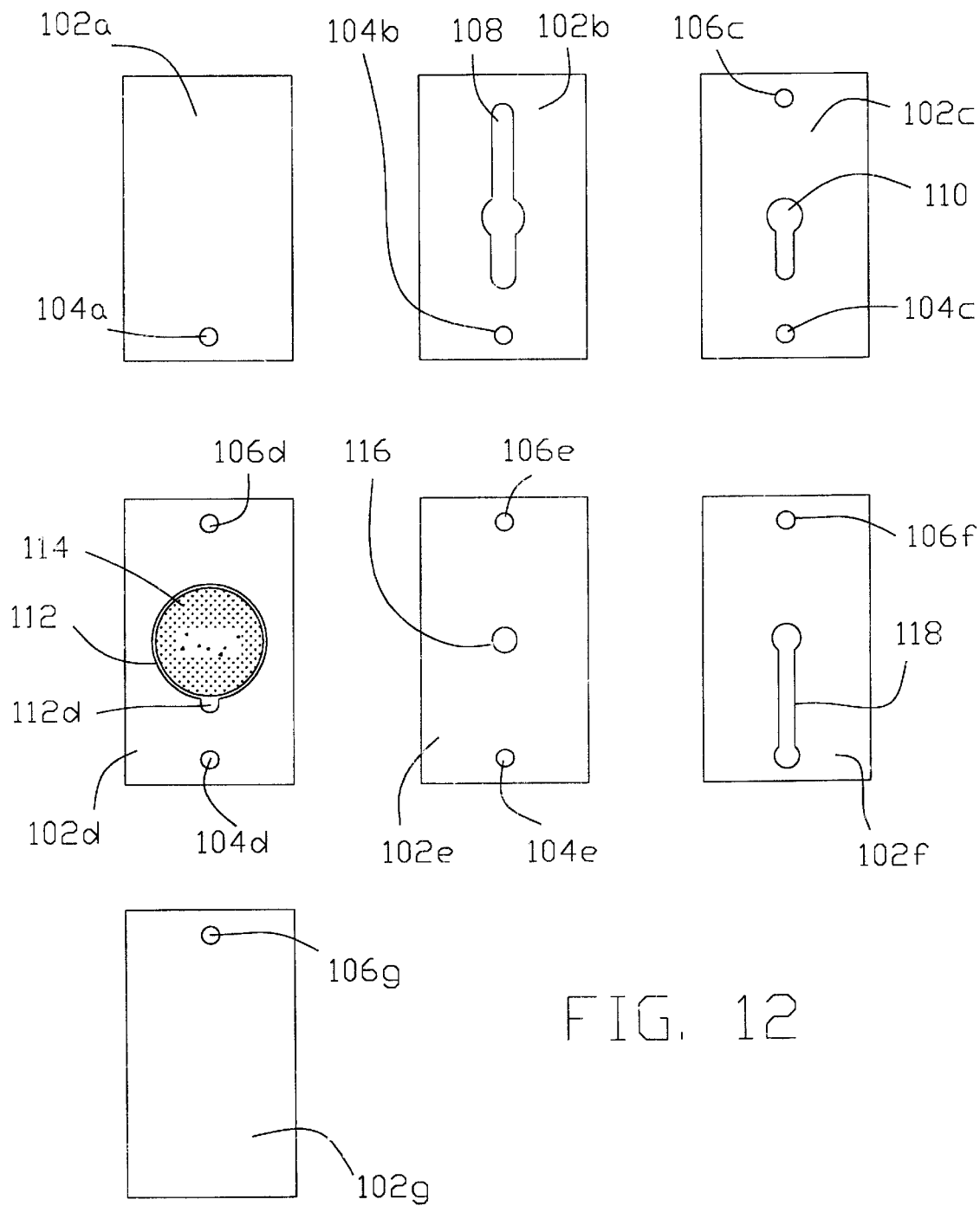
FIG. 12 is a top view of each of the individual layers of the valve shown in FIG. 7.

Referring now to FIGS. 4 and 5, recirculating pump 38 contains the same structure as the basic device shown in FIG. 1, having layers 12, 14, 16, 18 separated by spacing sheets 20a–c, 22a–c, 24a–c. A first check valve is created by flexible valve flap 34 formed from opening 35 in layer 14 and which contacts the underside of sheet 20c, while a second check valve is created by a flexible valve flap 40 formed from a second opening 41 within layer 14 and which contacts the upper side of sheet 22a. Chambers 30 and 32 remain isolated from each other when flaps 34 and 40 remain in the unactuated or closed position.

To operate pump 38, flexible top layer 12 is depressed as shown at arrow B, preferably by the finger of the pump operator. Pump 38 can also be designed such that an external mechanical apparatus, such as a solenoid, piezoelectric device, or an air pressure source is used to depress layer 12. Assuming that the fluid in chamber 30 is incompressible, valve flap 34 opens while valve flap 40 remains closed, and the volume in chamber 32 increases as fluid from chamber 30 travels through opening 35 as shown by arrow C while, layer 18 flexes to the position shown at arrow D. In theory, the expansion of chamber 32 will equal the compression of chamber 30 in amplitude and volume, assuming that layers 12 and have an identical radius.

When layer 12 is released, it returns to its initial at-rest position as shown by arrow E, and valve flap 34 closes. Layer 18 also returns to its initial position, which forces valve flap 40 open, allowing fluid from chamber 32 to flow back through opening 41 into chamber 30 along the path shown by arrow F. The force exerted on the fluid by the relaxation of layer 12 is equal to the force-deforming chamber 30 by depressing layer 12.

Pumps such as pump 38 are important in the design of microfluidic devices. The ability to keep fluids moving within a microfluidic structure is important for mixing and anti-sedimentation. The analysis of whole blood within a microfluidic structure may require cells to remain suspended within a reaction chamber or flow injector. Recirculation pumping is a means for maintaining suspension or particles within fluids.

Figure 6:
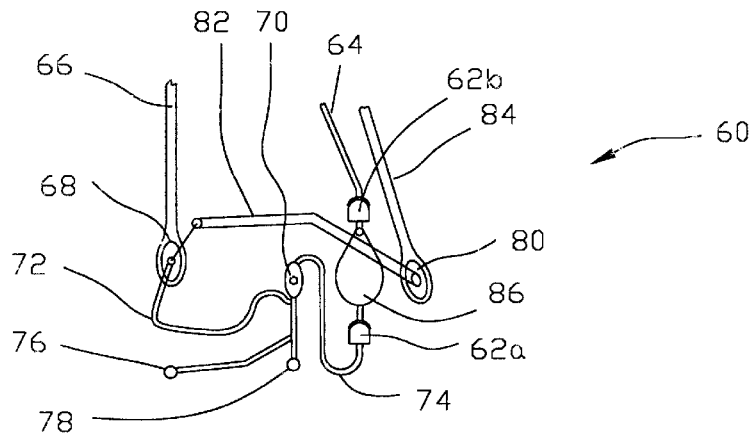
FIG. 6 is a top view of a recirculating system within a microfluidic device which includes check valves according to the present invention.
Figure 9:
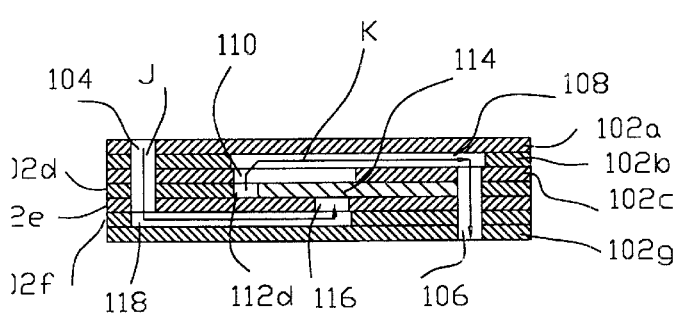
FIG. 9 is a side view, shown in cross-section, of the valve shown in FIG. 7.
Figure 10:
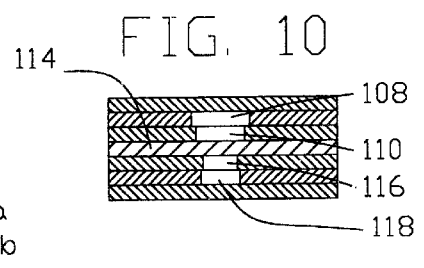
FIG. 10 is an end view, shown in cross-section, of the valve shown in FIG. 7 in its unactivated state.
Figure 11:
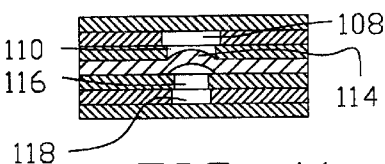
FIG. 11 is an end view, shown in cross-section, of the valve shown in FIG. 7 in its activated state.

FIG. 6 shows the layout of a recirculating microfluidic design which includes check valves constructed according to the present invention. Referring now to FIG. 6, there is shown a microfluidic circuit 60 containing a recirculating pump using check valves 62. This circuit may be utilized to mix two fluids together in a precise ratio defined by the two microfluidics channel volumes in which these fluids are captured. An outlet line 64 and an inlet line 66 of the recirculating loop connect to a known fixed volume circuit. The circuit may be used to sense reaction, divert the mixed solution, or merely hold the necessary volume of reagent fluid to be mixed.

In operation, inlet line 66 is coupled to a conventional two-way valve 68, which valve is connected to a valve 70 via a sample storage by channel 72. Valve 70 is coupled to inlet check valve 62a of the present invention via a pump feed channel 74. Valve 70 is also connected to a sample port inlet 76 and a reagent port inlet 78. Valve 68 is also coupled to a valve 80 via a waste connector channel 82, while valve 80 is also coupled to a waste channel 84. Finally, a pump bellows 86 couples check valves 62a and 62b together, while valve 62b is connected to outlet line 64.

The process for loading and recirculating circuit 60 is as follows: inlet 78 receives a feed of sample fluid to be analyzed. Valves 68 and 70 are closed prior to the sample load, preventing sample fluid from entering channel 74 or inlet 66. Valve 80 remains open, allowing sample fluid to flow within channel 82 and out through waste channel 84. A reagent is then introduced through inlet 78 to valve 70. As valve 70 is closed, the reagent remains isolated from the sample fluid. Reagent fills pump feed channel 74 through check valve 62a, pump bellows 86 and through check valve 62b into outlet line 64 into other circuitry, and back into circuit 60 via inlet line 66 to valve 68. Valve 68 is then opened while valve 70 is kept closed, thus forcing reagent out of channel 82 through open valve 80 and out through waste channel 84. This process traps a fixed volume of reagent within circuit 60.

At this point valve 80 is closed and valves 68 and 70 are opened. Bellows 86 is activated, forcing fluid out of bellows 86 through valve 62b and into the compliance of outlet line 64 (and associated sensor circuitry) and inlet line 66. This pumping action of bellows 86 forces check valve 62a closed. Bellows 86 is then released, and as the pressure is removed from the chamber of bellows 86, check valve 62a now opens as check valve 62b closes, sweeping a pulsed volume of fluid into bellows 86. This process is then repeated multiple times, until mixing, dilution, or sensing is complete.

Another example of a check valve embodying the principles of the present invention is shown in FIGS. 7–12. Referring now to FIG. 7, a check valve assembly, generally indicated at 100, is shown having a series of laminated layers 102a–g, along with a pair of channels 104 and 106, with channel 104 exiting assembly 100 through top layer 102a and channel 106 exiting assembly 100 through bottom layer 102g. Top layer 102b contains an aperture 104b which is aligned with aperture 104a, along with a cutout section 108 forming a channel between layers 102a and 102c. Layer 102d contains an aperture 104d aligned with aperture 104c, an aperture 106c which is aligned with aperture 106c, and a cutout section 112. Section 112 includes a region 112d aligned with section 110 of layer 102c, and also contains an elastomeric insert 114 which is held captive within section 112 between layers 102c and 102e. Insert 114 is preferably constructed from latex or another similar material. Layer 102e contains an aperture 104e aligned with aperture 104d, an aperture 106e aligned with aperture 106d, and an aperture 116 aligned with section 112 of layer 102d. Layer 102f contains an aperture 106f aligned with aperture 106e and a cutout section 118 which is aligned at one end with aperture 116 of layer 102e and at its other end with aperture 104e of layer 102e. Finally, layer 102g contains an aperture 106g aligned with aperture 106f j of layer 102f.

Layers 102a, 102c, 102e, and 102g are preferably constructed from MYLAR in this embodiment, while layers 102b, 102d, 102f are preferably constructed from Adhesive Carrier Adhesive (ACA) material manufactured by 3M Company.

Having described the elements of valve assembly 100 of the present invention, the operation of the embodiment will now be described. Referring now to FIGS. 7, 9, 10 and 11, liquid pressure is applied in channel 104 in the direction of arrow J. Channel 104, which is formed by aperture 104a, 104b, 104c, 104d, and 104e, communicates with cutout section 118 in layer 102f. Liquid flows through channel 104, along cutout channel section 118, and upward through aperture 116 of layer 102e, to elastomeric insert 114. A sufficient minimum liquid pressure causes insert 114 to stretch, as can be seen most clearly in FIG. 11. When insert 114 stretches to the position shown in FIG. 11, liquid travels through region 112d within layer 102d, through section 110, and into channel section 108, as shown by arrow K in FIG. 9, and finally into channel 106, where it exits valve assembly 100.

If liquid pressure is applied in the reverse direction through channels 106 and 108, this pressure forces elastomeric insert 114 against the flat surface of layer 102e, effecting a seal against the flow of the liquid. Thus, the elastic property of insert 114 allows for sealing valve assembly 100 during reverse flow, as well as biasing valve assembly 100 to a normally closed position when no pressure is present within assembly 100. Insert 114 is biased to its open or operating position only where a minimum pressure is applied in the forward direction.

Another embodiment of this invention provides an array of the valves of the types described in FIGS. 1–6, and FIGS. 7–12, respectively. Such an array of microfluidic check valves can be integrated into a cartridge constructed of multi-layer laminates, and can be used to control multiple parallel fluidic processes, or a single process at multiple locations in the microfluidic circuit. Such as system may have applications in drug discovery processes, or in the analysis of multiple samples.

While this invention has been shown and described in terms of a preferred embodiment, it will be understood that this invention is not limited to any particular embodiment and that changes and modifications may be made without departing from the true spirit and scope of the invention as defined in the appended claims.

What is claimed is:

1. A microfluidic structure, comprising:
   a first layer of flexible material having a top side and a bottom side;
   a second layer of flexible material having a top side and a bottom side;
   a first spacing layer contacting said bottom side of said first layer and said top side of said second layer for separating said first and second layers, forming a first microfluidic channel;
   a third layer of flexible material having a top side and a bottom side;
   a second spacing layer contacting said bottom side of said second layer and said top side of said third layer for separating said second and third layers forming a second microfluidic channel;
   wherein said second layer contains an opening forming an actuator section within said second layer, said actuator section shiftable between a first unactuated position in contact with said first spacing layer such that said first and second microfluidic channels are isolated from each other and a second actuated position such that said first and second microfluidic channels are in fluid communication with each other.

2. The structure of claim 1, wherein said first spacing layer comprises a plurality of thin flexible materials.

3. The structure of claim 1, wherein said first, second, and third layers are constructed from MYLAR.

4. The structure of claim 1, wherein the volume of said first microfluidic channel and said second microfluidic channel are equal.

5. The structure of claim 1, further comprising a plurality of openings within said second layer and a plurality of said first and second microfluidic channels whereas said openings form a plurality of said actuator sections shiftable between a first unactuated position in contact with said first spacing layer such that said first and second microfluidic channels are isolated from each other and a second actuated position such that said plurality of said first and second microfluidic channels are in fluid communication with each other.

6. The structure of claim 5, further comprising means to individually actuate said actuator sections.

7. The structure of claim 6, wherein said means to individually actuate said actuator sections is taken from a group consisting of hydraulic, mechanic, pneumatic, magnetic, and electrostatic actuators.

8. A recirculating pump for use in a microfluidics structure, comprising:

a first layer of flexible material having a top side and a bottom side;

a second layer of flexible material having a top side and a bottom side;

a first spacer contacting said bottom side of said first layer and said top side of said second layer for separating said first and second layers, forming a first microfluidic channel;

a third layer of flexible material having a top side and a bottom side;

a second spacer contacting said bottom side of said second layer and said top side of said third layer for separating said second and third layers, forming a second microfluidic channel;

wherein said second layer contains: a first slit forming a first actuator in said second layer, said first actuator shiftable between a first unactuated position in contact with said first spacer in which said first and second channels are isolated from one another and a second actuated position in which said first and second channels are in fluid communication with each other, and a second slit forming a second actuator in said second layer shiftable between a first unactuated position in contact with said second spacer in which said first and second channels are isolated from one another and a second actuated position in which said first and second channels are in fluid communication with each other;

and activating means for shifting said first layer to a first pumping position from its normal position;

whereby when said first layer is shifted to said first pumping position, said first actuator is shifted to said second actuated position while said second actuator is in said first unactuated position, thus forcing fluid from said first microfluidic channel into said second microfluidic channel.

9. The pump of claim 8, wherein when said first layer is shifted to said first pumping position, said third layer is shifted from a first unactuated position to a second actuated position.

10. The pump of claim 8, wherein the volume of said first and second microfluidic channels is equal.

11. The pump of claim 9, wherein when said first layer returns from said first pumping position to its normal position, said first actuator is shifted to its first unactuated position while said second actuator is shifted to its second actuated position, thus forcing fluid from said second microfluidic channel into said first microfluidic channel.

12. The pump of claim 11, wherein continued sequential activation of said activating means causes fluid to circulate continuously from said first microfluidic channel to said second microfluidic channel and back to said first microfluidic channel.

13. The pump of claim 8, wherein said first and second layers are constructed from MYLAR.

14. The pump of claim 8, wherein said activating means is located external to the pump.

15. The pump of claim 14, wherein said activating means comprises an operator physically depressing said first layer manually.

16. The pump of claim 8, wherein said activating means comprises an air pressure source.

17. The pump of claim 8, wherein said activating means comprises an electromagnetic force generating mechanism.

18. The pump of claim 17, wherein said electromagnetic force generating mechanism comprises a solenoid.

19. The pump of claim 8, wherein said activating means comprises an electrostatic force generating mechanism.

20. The pump of claim 19, wherein said electrostatic force generating means comprises a piezoelectric device.

21. A microfluidic device, comprising:

a valve structure;

a microfluidic inlet channel formed within said valve structure;

a microfluidic outlet channel formed within said valve structure;

an elastomeric structure separating said inlet and said outlet channels having a first unactuated position isolating said inlet channel from said outlet channel and a second actuated position whereby said inlet and said outlet channels are in fluid communication with each other, whereby when a fluid is introduced into said inlet channel, pressure within said inlet shifts said elastomeric structure from said first unactuated position to said second actuated position allowing fluid to flow from said inlet channel to said outlet channel, and when a fluid is introduced into said outlet channel, pressure holds said elastomeric structure in said first unactuated position, preventing flow between said inlet and outlet channels.

* * * * *